United States Patent [19]

Axelsson et al.

[11] Patent Number: 4,693,999

[45] Date of Patent: Sep. 15, 1987

[54] LIPOSOMES CONTAINING STEROID ESTERS

[75] Inventors: Bengt I. Axelsson, Genarp; Ralph L. Brattsand; Carl M. O. Dahlbäck, both of Lund; Leif A. Källström, Södra Sandby; Jan W. Trofast, Lund, all of Sweden

[73] Assignee: Aktiebolaget Draco, Sweden

[21] Appl. No.: 752,257

[22] Filed: Jul. 3, 1985

[30] Foreign Application Priority Data

Jul. 30, 1984 [SE] Sweden ................... 8403905

[51] Int. Cl.$^4$ ............... A61K 31/56; A61K 31/58; C07J 00/00

[52] U.S. Cl. ............... 514/174; 260/397.1; 260/397.45; 514/180; 540/63; 540/70

[58] Field of Search ............... 260/397.45, 397.1; 514/180, 174; 540/63, 70

[56] References Cited

U.S. PATENT DOCUMENTS

| 4,229,360 | 10/1980 | Schneider et al. | 260/403 |
| 4,247,411 | 1/1981 | Vanlerbergbe | 260/403 |
| 4,427,649 | 1/1984 | Dingle et al. | 514/280 |

FOREIGN PATENT DOCUMENTS

| 0041772 | 5/1981 | European Pat. Off. | 514/180 |
| 3228629 | 2/1984 | Fed. Rep. of Germany | 260/397.2 |
| 0378109 | 8/1975 | Sweden | 514/180 |
| 1523965 | 9/1978 | United Kingdom | 514/180 |
| 1575343 | 9/1980 | United Kingdom | 260/397.45 |
| 2135647 | 9/1984 | United Kingdom | 260/403 |

OTHER PUBLICATIONS

Chem. Abstracts, vol. 92, No. 5, Par. 34888k.

*Primary Examiner*—Leonard Schenkman
*Attorney, Agent, or Firm*—Brumbaugh, Graves, Donohue & Raymond

[57] ABSTRACT

Pharmaceutical composition for administration primarily to the respiratory tract when treating and controlling anti-inflammatory conditions comprising liposomes in combination with a compound of the formula $$Q-OC(=O)-R^1 \quad I$$

wherein Q is

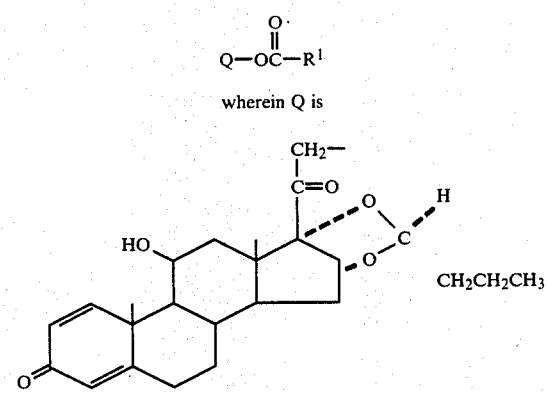

-continued

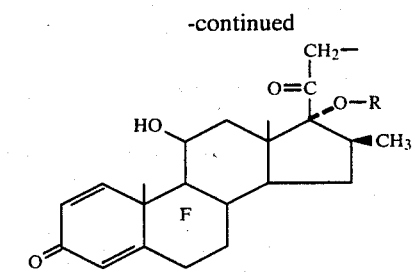

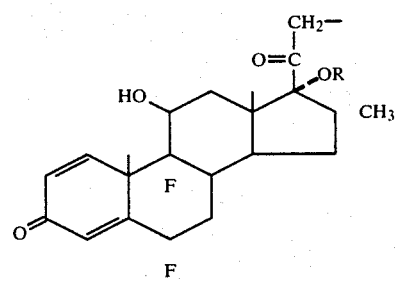

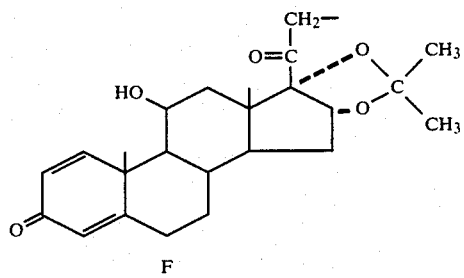

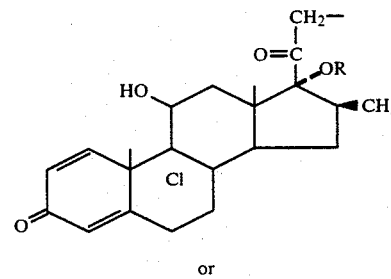

or

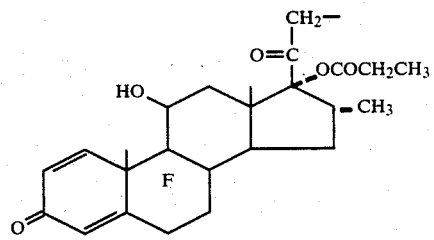

and $R^1$ is a saturated or unsaturated, straight or branched alkyl group with 11-19 carbon atoms and R is H, —COCH$_3$, —COC$_2$H$_5$, —CO(CH$_2$)$_2$CH$_3$ or —CO(CH$_2$)$_3$CH$_3$.

The invention also refers to the compounds of the formula I per se processes for preparation of these compounds and to a method for the treatment of inflammatory conditions.

7 Claims, No Drawings

LIPOSOMES CONTAINING STEROID ESTERS

DESCRIPTION

1. Field of the Invention

The present invention relates to anti-flammatory and antiallergic pharmaceutical compositions containing liposomes including pharmacologically active steroid esters, the steroid esters per se, processes for the preparation of the compositions and the esters and to methods of the pharmacological use of the compositions.

The object of the invention is to provide an anti-inflammatory and antiallergic pharmaceutical composition containing a liposome-incorporated steroid ester for the local administration e.g. to the respiratory tract and thus obtaining a prolongation of the local retention of the drug and to direct the drug to specific target cells.

2. Background Art

It is well-known that phospholipids, when suspended in an excess of aqueous solution, spontaneously forms multilamellar vesicles. Liposomes have been used as carriers for different kinds of pharmaceutically active compounds in order to improve drug delivery and to minimize side effects of the therapy. For this purpose steroid esters have been combined with liposomes as well.

Biochem. J. (1976) 158, 473–476 describes the combination of hydrocortisone palmitate and octanoate with liposomes for use in treatment of rheumatoid arthritis.

Agents and Actions, vol. 12, 3 (1982) describes hydrocortisone palmitate liposomes and the anti-inflammatory effect thereof.

Dexamethasone-21-palmitate has been reported to be given as a fat emulsion in the treatment of arthritis (EP 41772).

Synthesis and spectroscopic properties of dexamethasone-21-linoleate and dexamethasone-21-linolelaidate are reported and discussed (Arzneim.-Forsch. 26(1) 7 (1976).

International Journal of Pharmaceutics, 16 (1983), 305–318 describes the interaction of cortisone esters with liposomes.

DE No. 2712030 discloses administration of liposomes containing certain steroids directly into an enclosed cavity. Liposomes for inhalation is otherwise only described in connection with compositions of liposomes and sodium chromoglycate (EP No. 84898).

3. Disclosure of the Invention

Liposomes administered by a systemic route is mainly retained by the liver, but also the spleen and the lung show a significant degree of retention (Chem. Pharm. Bull. 30, (6), 2248–2251 (1982)). The usefulness of this form of administration is therefore limited when an anti-inflammatory and antiallergic effect primarily in the respiratory tract is intended.

According to the invention an anti-inflammatory and antiallergic pharmaceutical composition containing steroid ester liposomes for local administration primarily to the respiratory tract is described.

The composition according to the invention provides for an improvement of the therapeutic properties of the steroid ester by a prolongation of the local retention in the airways and a direction of the drug to specific target cells.

More particular, the present invention is concerned with a pharmaceutical composition comprising liposomes containing novel esterified glucocorticoids.

The novel esterified glucocorticoids are characterized by the general formula

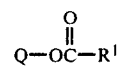

wherein Q is

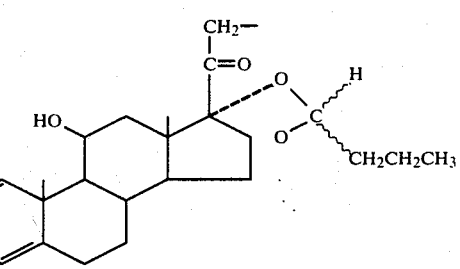

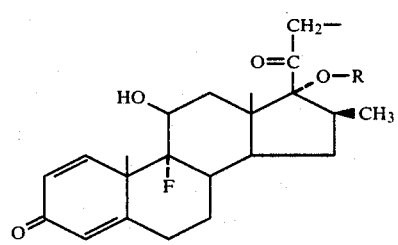

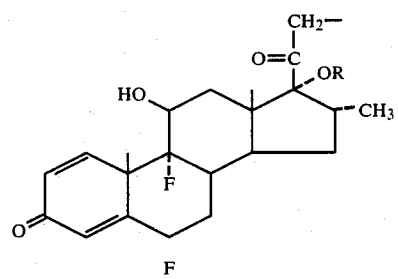

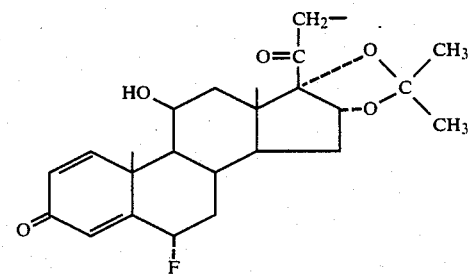

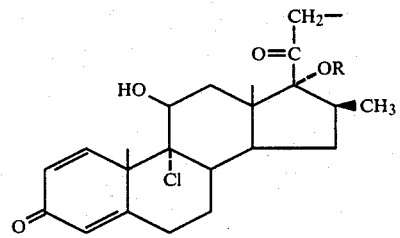

or

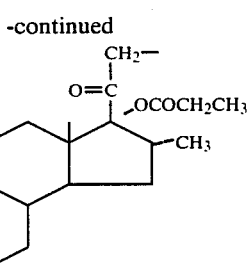

$R^1$ is a saturated or unsaturated, straight or branched alkyl group with 11–19 carbon atoms and R is H, —COCH$_3$, —COC$_2$H$_5$, —CO(CH$_2$)$_2$CH$_3$ or —CO(CH$_2$)$_3$CH$_3$.

The degree of inclosure of the steroid to the liposomes are enhanced by the esterification of the steroids in the 21-position.

The steroid esters of the formula I are new and constitute a part of the invention.

The preferred ester groups are moieties of
C$_{11}$H$_{23}$COCH: lauric acid;
C$_{13}$H$_{27}$COOH: myristic acid;
C$_{15}$H$_{31}$COOH: palmitic acid;
C$_{17}$H$_{35}$COOH: stearic acid;
C$_{17}$H$_{33}$COOH: oleic acid;
C$_{17}$H$_{31}$COOH: linolic acid;
C$_{17}$H$_{29}$COOH: linolenic acid;

The preferred steroid ester has the formula

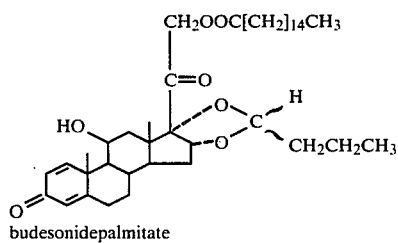

budesonidepalmitate

All budesonide esters can be obtained in two diastereomeric forms depending on the asymmetric carbon in position 22.

The steroid esters

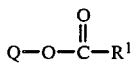

are prepared by one of the following alternative methods.

A. Reaction of a compound of the formula

wherein Q has the definition given above, with a compound of the formula

R$^1$COOH wherein R$^1$ has the definition given above.

The esterification of the 21-hydroxy compound may be effected in known manner e.g. by reacting the parent 21-hydroxy steroid with an appropriate carboxylic acid, advantageously in the presence of trifluoroacetic anhydride and preferably in the presence of an acid catalyst e.g. p-toluenesulphonic acid.

The reaction is advantageously effected in an organic solvent such as benzene or methylene chloride; the reaction being conveniently effected at a temperature of 20°–100° C.

B. Reaction of a compound of the formula

wherein Q has the definition given above, with a compound of the formula

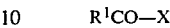

wherein R$^1$ has the definition given above and X is a halogen atom, such as chlorine, bromine, iodine and fluorine, or the group

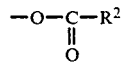

wherein R$^2$ has the same definition as R$^1$.

The parent 21-hydroxy compound may be treated with the appropriate carboxylic acid halide or anhydride, preferably in a solvent such as halogenated hydrocarbone e.g. methylene chloride and advantageously in the presence of a base such as triethylamine or pyridine, preferably at a low temperature e.g. −5° to +30° C.

C. Reaction of a compound of the formula

wherein Q has the definition given above and X$^1$ is a leaving group, with a compound of the formula

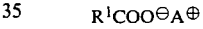

wherein R$^1$ has the definition given above and A$^\oplus$ is a cation.

A salt of the appropriate carboxylic acid, for example, an alkali metal e.g. lithium, sodium or potassium salt or a triethylammonium or tetrabutyl ammonium salt may be reacted with the appropriate alkylating agent of the formula Q—X$^1$ where Q is the same as above and X$^1$ is a leaving group such as Cl, Br, I, mesylate or p-toluenesulphonate, preferably in a polar solvent such as acetone, methylethyl ketone or dimethyl formamide, conveniently at a temperature in the range 25°–100° C.

PREPARATION OF THE COMPOSITION ACCORDING TO THE INVENTION

The lecithins used in this invention have fatty acid chains of different lengths and therefore have different phase-transition temperatures. Examples of lecithins used are those derived from egg and soybean and synthetic lecithins like dimyristoyl phosphatidylcholine (DMPC), dipalmitoyl phosphatidylcholine (DPPC) and distearoyl phosphatidylcholine (DSPC). By manipulation of the structure lecithins stable carriers with variable biodegradable properties could be formulated. This would enable one to prolong the release of the entrapped steroid ester.

The extent of the interaction of the steroid ester with e.g. dipalmitoylphosphatidylcholine (DPPC) vesicles is dependent on the ester chain length with increased interaction observed as the chain lengthens.

The inclusion of cholesterol or cholesterol derivatives in liposome formulations has become very common due to its properties in increasing liposome stability.

The initial stages of the preparation of liposomes according to the present invention may conveniently follow procedures described in the literature i.e. the components being dissolved in a solvent e.g. ethanol or chloroform which is then evaporated. The resulting lipid layer is then dispersed in the selected aqueous medium whereafter the solution is either shaken or sonicated. The liposomes of this invention preferably have a diameter of between 0.1 and 10 μm.

In addition to the main liposome-forming lipid(s) which is usually phospholipid, other lipids (e.g. cholesterol or cholesterol stearate) in the amount of 0–40% w/w of the total lipids may be included to modify the structure of the liposome membrane. In optimizing the uptake of the liposome a third component providing a negative charge (e.g. phosphatidic acid) or a positive charge (e.g. stearylamine acetate or cetylpyridinium chloride) may be incorporated.

A wide range of proportions of steroid ester to lipid during formation may be used depending on the lipid and the conditions used. Drying, (freeze-drying or spray drying) of the liposomes in the presence of lactose can be used with a lactose content in the range of 0 to 95% of the final composition.

The composition according to the invention which is particularly preferred contains liposomes and budesonide-21-palmitate. The routes of administration involves powder aerosols, instillation, nebulization and pressurized aerosols.

WORKING EXAMPLES

Steroid esters

The invention is further illustrated by the following examples to which it is not limited. All the mass spectra have been obtained by chemical ionization mass spectrometry ($CH_4$-gas) and they are all in agreement with the molecular weights of the compounds. The purity of each compound has been determined on a HPLC (High Performance Liquid Chromatography) system using a μBondapak $C_{18}$ column (300×3.9 mm i.d.) with a flow rate of 1.0 ml/min and with ethanol/$H_2O$ in ratio between 70:30 and 90:10 as the mobile phase.

EXAMPLE 1

Budesonide-21-palmitate (Method B)

Budesonide (1 mmole) was dissolved in pyridine (20 ml). Palmitoyl chloride (2 mmole) was added at 0° C. and then at ambient temperature overnight. While cooling the mixture with ice 2M hydrochloric acid was added until acidic reaction. The mixture was extracted with chloroform (3×50 ml). The organic phase was successively shaken with 5% sodium bicarbonate and water, dried ($Na_2SO_4$) and evaporated. The raw material was purified by preparative thin layer chromatography (Silica gel; 3% EtOH: 97% $CHCl_3$). Yield: 40%. Purity: 95.5%. MS-CI ($CH_4$): $MH^+ = 669$, $M^+ + 29 = 697$.

EXAMPLE 2

Budesonide-21-laurate (Method B)

Reaction of budesonide (0.5 mmole) with lauryl chloride (0.25 ml) in pyridine (3 ml) according to Example 1 gave after preparative thin-layer chromatography (Silica gel; 3% EtOH: 97% $CHCl_3$) the title compound. Yield: 47%. MS-CI ($CH_4$): $MH^+ = 613$, $M^+ + 29 = 641$.

EXAMPLE 3

Budesonid-21-myristate (Method B)

The myristoyl chloride was synthesized by refluxing myristic acid (7.0 g) and thionyl chloride (9 ml) in trichloroethylene (100 ml) for 3 hours. The solvent was then evaporated.

Budesonide (2 mmole) and myristoyl chloride (2.4 mmole) in methylene chloride (40 ml) was treated with triethylamine (2.4 mmole) in methylene chloride (10 ml) for 2 hours at room temperature. Methylene chloride was added and the organic phase was successively treated with 1M HCl and water (3×100 ml). Chromatography (Sephadex LH20; chloroform) after drying ($Na_2SO_4$) and evaporation of the solvent gave the title compound in 65% yield. Purity: 98.2%. MS-CI ($CH_4$): $MH^+ 32\ 641$; $M^+ + 29 = 669$.

EXAMPLE 3b

Budesonide-21-myristate (Method C)

Budesonide-21-mesylate (0.5 mmole; prepared according to CA 57, 13842d (1962)), myristic acid (0.5 mmole) and triethylamine (0.5 mmole) in dimethylformamide (10 ml) was stirred for 2 hours at 50° C. The solvent was evaporated in vacuo and using the same work-up procedure as in method B gave after chromatography the title compound, identical with the compound isolated in method B.

EXAMPLE 3c

Budesonide-21-myristate (Method A)

Budesonide (1 mmole), myristic acid (1 mmole) and p-toluenesulfonic acid (5 mg) were refluxed in benzene (30 ml) for 5 hours. The organic phase was successively shaken with 5% sodium bicarbonate and water, dried ($Na_2SO_4$) and evaporated. Purification by preparative thin-layer chromatography gave the title compound, identical with the compound isolated in method B.

EXAMPLE 4

Budesonide-21-stearate (Method B)

Reaction of budesonide (1 mmole) with stearoyl chloride (1.0 ml) in pyridine (6 ml) according to Example 1 gave after preparative thin-layer chromatography (Silica gel; 3% EtOH: 97% $CHCl_3$) the title compound. Yield: 74%. MS-CI ($CH_4$): $MH^+ = 697$; $M^+ + 29 = 725$.

EXAMPLE 5

Budesonide-21-oleate (Method B)

Reaction of budesonide (1.16 mmole) and oleoyl chloride (1.4 mmole) in methylene chloride (50 ml) with triethylamine (1.4 mmole) in methylene chloride (5 ml) 2 hours at room temperature gave after work-up (Example 3) and chromatography (Silica gel; hexane-acetone (80:20)) the title compound in 22% yield. Purity: 98.7%. MS-CI ($CH_4$): $MH^+ = 695$; $M^+ + 29 = 723$.

EXAMPLE 6

Betamethasone-21-laurate (Method B)

Reaction of betamethasone (2 mmole) and lauryl chloride (2.4 mmole) in diemthylformamide (20 ml) with triethylamine (2.4 mmole) in diemthylformamide (5 ml) for 2 hours at room temperature gave after evaporation of dimethylformamide and work-up (Example 3) and chromatography (silica gel; hexane-acetone (60:40)) the title compound in 22% yield. Purity: 92.7%. MS-CI (CH$_4$): MH$^+$ =575; M$^+$ +29=603.

EXAMPLE 7

Betamethasone-21-myristate (Method B)

Reaction of betamethasone (2 mmole) and myristoyl chloride (2.4 mmole) in methylene chloride (40 ml) and diemthylformamide (5 ml) with triethylamine (2.4 mmole) in methylene chloride (10 ml) for 2 hours at room temperature gave after evaporation of dimethylformamide and work-up (Example 3) and chromatography (Silica gel; hexane-acetone (70:30)) the title compound in 29% yield. Purity: 97%. MS-CI (CH$_4$): MH$^+$ =603; M$^+$ +29=631.

EXAMPLE 8

Betamethasone-21-palmitate (Method B)

Reaction of betamethasone (0.5 mmole) with palmitoyl chloride (1.0 mmole) in pyridine (10 ml) according to Example 1 gave after preparative thin-layer chromatography (Silica gel 3%; EtOH: 97% CHCl$_3$) the title compound. Yield: 33%. MS-CI (CH$_4$): MH$^+$ =631; M$^+$ +29=659.

EXAMPLE 9

Betamethasone-21-oleate (Method B)

Reaction of betamethasone (2 mmole) and oleoyl chloride (3 mmole) in dimethylformamide (20 ml) with triethylamine (3 mmole) in dimethylformamide (5 ml) for 2 hours at room temperature gave after evaporation of dimethylformamide and work-up (Example 3) and chromatography (Sephadex LH20; chloroform) the title compound. Purity: 96.7%. MS-CI (CH$_4$): MH$^+$ =657; M$^+$ +29=685.

EXAMPLE 10

Betamethasone-21-laurate-17-valerate (Method B)

Reaction of betamethasone-17-valerate (2 mmole) and lauroyl chloride (2.4 mmole) in methylene chloride (90 ml) with triethylamine (2.4 mmole) in methylene chloride (10 ml) for 2 hours at room temperature gave after work-up (Example 3) and chromatography (Sephadex LH20; chloroform) the title compound in 62% yield. Purity: 97.8%. MS-CI (CH$_4$): MH$^+$ =659; M$^+$ +29=687.

EXAMPLE 11

Betamethasone-21-myristate-17-valerate

Reaction of betamethasone-17-valerate (2 mmole) and myristoyl chloride (2.4 mmole) in methylene chloride (90 ml) with triethylamine (2.4 mmole) in methylene chloride (10 ml) for 2 hours at rooom temperature gave after work-up (Example 3) and chromatography (Sephadex LH20; chroroform) the title compound in 62% yield. Purity: 95.5%. MS-CI (CH$_4$): MH$^+$ =687; M$^+$ +29=715.

EXAMPLE 12

Betamethasone-21-palmitate-17-valerate

Reaction of betamethasone-17-valerate (1 mmole) and palmitoyl chloride (1.2 mmole) in methylene chloride (50 ml) with triethylamine (1.2 mmole) in methylene chloride (10 ml) for 2 hours at room temperature gave after work-up (Example 3) and chromatography (Sephadex LH20; chroroform) the title compound in 63% yield. Purity: 95.9%. MS-CI (CH$_4$): MH$^+$ =715; M$^+$ +29=743.

EXAMPLE 13

Betamethasone-21-stearate-17-valerate (Method B)

Reaction of betamethasone-17-valerate (2 mmole) and stearyl chloride (2.4 mmole) in methylene chloride (90 ml) with triethylamine (2.4 mmole) in methylene chloride (10 ml) for 2 hours at room temperature gave after work-up (Example 3) and chromatography (Sephadex LH-20; chloroform:heptane:ethanol (20:20:1)) the title compound in 59% yield. Purity: 92%. MS-CI (CH$_4$): MH$^+$ =743; M$^+$ +29=771.

EXAMPLE 14

Flumethasone-21-laurate (Method B)

Reaction of flumethasone (1.0 mmole) and lauroyl chloride (1.5 mmole) in dimethylformamide (5 ml) and methylene chloride (40 ml) with triethylamine (1.5 mmole) in methylene chloride for 2 hours at room temperature gave after evaporation of dimethylformamide and work-up (Example 3) and chromatography (Silica gel; hexane:acetone (70:30)) the title compound in 64% yield. Purity: 97.7%. MS-CI (CH$_4$): MH$^+$ =593; M$^+$ +29=621.

EXAMPLE 15

Flumethasone-21-palmitate (Method B)

Reaction of flumethasone (0.5 mmole) with palmitoyl chloride (1.0 mmole) in pyridine (10 ml) according to Example 1 have after preparative thin-layer chromatography (Silica gel; 3% EtOH: 97% CHCl$_3$) the title compound. Yield: 38%. Purity: 98.5%. MS-CI (CH$_4$): MH$^+$ =649; M$^+$ +29=677.

EXAMPLE 16

Flumethasone-21-stearate (Method B)

Reaction of flumethasone (1.0 mmole) and stearoyl chloride (1.5 mmole) in dimethylformamide (5 ml) and methylene chloride (40 ml) with triethylamine (1.5 mmole) in methylene chloride (10 ml) gave after evaporation of dimethylformamide and work-up (Example 3) and chromatography (Silica gel; hexane:acetone (70:30)) the title compound in 38% yield. Purity: 90%. MS-CI (CH$_4$): MH$^+$ =677.

EXAMPLE 17

Flumethasone-21-oleate (Method B)

Reaction of flumethaosne (1.0 mmole) and oleoyl chloride (1.5 mmole) in dimethylformamide (5 ml) and methylene chloride (40 ml) with triethylamine (1.5 mmole) in methylene chloride (10 ml) gave after evaporation of dimethylformamide and work-up (Example 3) and chromatography (Silica gel; hexane:acetone (70:30)) the title compound in 12% yield. Purity: 98.2%. MS-CI (CH$_4$): MH$^+$ =675; M$^+$ +29=703.

EXAMPLE 18

Flumethasone-21-laurate-17-propionate (Method B)

Reaction of flumethasone-17-propionate (1 mmole) and lauroyl chloride (1.5 mmole) in methylene chloride (40 ml) with triethylamine (1.5 mmole) in methylene chloride (10 ml) gave after work-up (Example 3) and chromatography (Silica gel; hexane:acetone (70:30)) the title compound in 33% yield. Purity: 94.4%. MS-CI (CH$_4$): MH$^+$=649; M$^+$+29=677.

EXAMPLE 19

Flumethasone-21-myristate-17-propionate (Method B)

Reaction of flumethasone-17-propionate (1 mmole) and myristoyl chloride (1.7 mmole) in methylene chloride (40 ml) with triethylamine (1.7 mmole) in methylene chloride (10 ml) gave after work-up (Example 3) and chromatography (Silica gel; hexane:acetone (70:30)) the title compound in 55% yield. Purity: 96.7%. MS-CI (CH$_4$): MH$^+$=677.

EXAMPLE 20

Flumethasone-21-palmitate-17-propionate (Method B)

Reaction of flumethasone-17-propionate (2.8 mmole) and palmitoyl chloride (3.3 mmole) in methylene chloride (150 ml) with triethylamine (3.3 mmole) in methylene chloride (10 ml) gave after work-up (Example 3) and chromatography (Sephadex LH20; chloroform) the title compound in 14% yield. Purity: 98.8%. MS-CI (CH$_4$): MH$^+$=705; M$^+$+29=733.

EXAMPLE 21

Flumethasone-17-propionate-21-stearate (Method B)

Reaction of flumethasone-17-propionate (1.0 mmole) and stearoyl chloride (1.5 mmole) in methylene chloride (40 ml) with triethylamine (1.5 mmole) in methylene chloride (10 ml) gave after work-up (Example 3) and chromatography (Silica gel; hexane:acetone (70:30)) the title compound in 44% yield. Purity: 95%. MS-CI (CH$_4$): MH$^+$=733; M$^+$+29=761.

EXAMPLE 22

Flunisolide-21-laurate (Method B)

Reaction of flunisolide (0.5 mmole) and lauroyl chloride (0.64 mmole) in methylene chloride (20 ml) with triethylamine (0.64 mmole) in methylene chloride (5 ml) gave after work-up (Example 3) and chromatography (Silica gel; hexane:acetone (70:30)) the title compound in 65% yield. Purity: 97.6%. MS-CI (CH$_4$): MH$^+$=612; MH$^+$=612; M$^+$+29=645.

EXAMPLE 23

Flunisolide-21-myristate (Method B)

Reaction of flunisolide (0.5 mmole) and myristoyl chloride (0.65 mmole) in methylene chloride (20 ml) with triethylamine (0.65 mmole) in methylene chloride (5 ml) gave after work-up (Example 3) and chromatography (Silica gel; hexane:acetone (60:40)) the title compound in 54% yield. Purity: 98.5%. MS-CI (CH$_4$): MH$^+$=645; M$^+$+29=673.

EXAMPLE 24

Flunisolide-21-palmitate (Method B)

Reaction of flunisolide (433 mg), palmitoyl chloride (400 mg) and triethylamine (500 mg) in methylene chloride (8 ml for 2 hours at room temperature gave after work-up (Example 3) and preparative thin-layer chromatography (Silica gel; chloroform) the title compound in 29% yield. Purity: 98.5%. MS-CI (CH$_4$): MH$^+$=673; M$^+$+29=701.

EXAMPLE 25

Flunisolide-21-stearate (Method B)

Reaction of flunisolide (0.46 mmole) and stearoyl chloride (0.7 mmole) in methylene chloride (40 ml) with triethylamine (0.7 mmole) in methylene chloride (10 ml) gave after work-up (Example 3) and chromatography (Silica gel; hexane:acetone (70:30)) the title compound in 53% yield. Purity: 92%. MS-CI (CH$_4$): MH$^+$=701; M$^+$+29=729.

EXAMPLE 26

Beclomethasone-21-palmitate-17-propionate (Method B)

Reaction of beclomethasone-17-propionate (40 mg), palmitoyl chloride (100 mg) and triethylamine (50 mg) in methylene chloride (5 ml) for 2 hours at room temperature gave after work-up (Example 3) and preparative thin-layer chromatography (Silica gel; 3% EtOH: 97% CHCl$_3$) the title compound in 54% yield. MS-CI (CH$_4$): MH$^+$=703.

EXAMPLE 27

Dexamethasone-21-palmitate-17-propionate (Method B)

Reaction of dexamethasone-17-propionate (4 mmole) and palmitoyl chloride (8 mmole) in methylene chloride (100 ml) with triethylamine (8 mmole) in methylene chloride (30 ml) for 2 hours at room temperature gave after work-up (example 3) and chromatography (Sephadex LH20; heptane:chloroform:ethanol (20:20:1)) the title compound in 25% yield. Purity: 96%. MS-CI (CH$_4$): MH$^+$=687; M$^+$+29=715.

Compositions

EXAMPLE 1

Preparation of a formulation for instillation

Synthetic dipalmitoylphosphatidylcholine (45 mg), cholesterol (2.25 mg) and budesonide-21-palmitate (4.5 mg) are mixed in a glass tube. All components are dissolved in chloroform. Most of the solvent is evaporated by the use of N$_2$ and then under reduced pressure, which forms a thin film of the lipid components on the surface of the glass tube. An aqueous solution (0.9% NaCl) is added to the lipids. Formation of the liposomes is performed at a temperature above the phase transition temperature of the lipids. The liposomes are formed by shaking or sonication of the solution with the probe of a sonicator. The resulting suspension contains liposomes ranging from very small vesicles to 2 μm in size.

EXAMPLE 2

Preparation of a formulation for inhalation

The preparation of the liposomes is performed according to Example 1, where the aqueous solution contains 10% lactose. The ratio between lactose and lipid is 10:1. The liposome suspension is frozen on dry ice and lyophilized. The dry product is micronized resulting in particles with a mass mean aerodynamic diameter (MMAD) of about 2 μm.

BIOLOGICAL TESTS

Anti-inflammatory effect

Intratracheal instillation of Sephadex beads into rats leads to bronchial and also to alveolar inflammation.

This provokes interstitial lung edema, which increases the lung weight, and the inflammation can be graded as the increase of the lung weight compared to a saline-instilled control group. The lung edema formation can be counteracted by pretreatment with glucocorticoids, preferably by local administration as intratracheal instillation or as inhalation. Ideally an anti-inflammatory action should be obtained only at the site of glucocorticoid application in the lung, but not in the rest of the body as this in long term treatment can lead to therapy limiting systemic side effects.

The differentiation between glucocorticoid actions in the treated lung region and outside this area can be tested in the following way.

Sprague Dawley rats (225 g) were slightly anaesthetized with ether and the glucocorticoid test preparation (in liposomes suspended in saline) in a volume of 0.5 ml/kg was instilled into just the left lung lobe. Two h later a suspension of Sephadex (5 mg/kg in a volume of 1 mg/kg was instilled in the trachea well above the bifurcation so that the suspension reached both the left and right lung lobes. Twenty h later the rats were killed and the left and right lung lobes dissected out and weighed separately. Also the spleen weight and the body weight gain over the 20 h were determined. Control groups got vehicle instead of glucocorticoid preparation and saline instead of Sephadex suspension to determine the weight of non-drug treated Sephadex edema and the normal lung weight as well as the normal spleen weight and body weight gain.

As stated above an ideal glucocorticoid preparation lated and compared with Student's t-test to the results of the corresponding Sephadex control group.

The results of the comparative studies are given in Table 1. The pharmacological profile of the new compounds was compared to that of budesonide (selected as a conventional glucocorticoid having some local activity as judged in skin tests) and to those of budesonide-21-valerate, dexamethasone-21-palmitate, fluocinolone acetonide-21-palmitate and hydrocortisone-21-palmitate (representing compounds outside the scope of the invention). Budesonide, budesonide-21-valerate and hydrocortisone-21-palmitate did not fulfil the requirement of a very high local activity (only up to 38% reduction of edema in left lung). Dexamethasone-21-palmitate and fluocinolone-21-palmitate completely blocked the left lung edema, but this was coupled to as high activity in the other lung half as well as to significant reduction of body weight gain and to spleen (Table 1). Thus, none of the tested preparations falling outside the scope of the invention had selective glucocorticoid activity for the site of application in lung.

The preparations of the new compounds of the invention had a much more selective activity for the application site in lung. They all more or less completely blocked the edema of the left lung (minimum 87% protection for beclomethasone-21-palmitate-17-propionate). This was surprisingly coupled to only a low or moderate protective activity in the other lung (maximally about 45% protection) and to no statistically significant reduction of body weight gain or spleen. Table 1.

TABLE 1

| Compound | Dose nmol/kg | Sephadex-included lung edema % inhib. compared to control group | | | Body weight gain in rel. to control |
|---|---|---|---|---|---|
| | | left lobe | right lobe | spleen | |
| Compounds of the invention | | | | | |
| Beclomethasone-21-palmitate-17-propionate | 3350 | 87* | 47 | 5 (NS) | −3.1 (NS) |
| Betamethasone-21-palmitate | 335 | 109* | −5 | 7 (NS) | 0.2 (NS) |
| Budesonide-21-palmitate | 335 | 100*** | 37*** | 4 (NS) | −1.4 (NS) |
| Dexamethasone-21-palmitate-17-propionate | 335 | 104** | 44 | 3 (NS) | 1.0 (NS) |
| Flumethasone-21-palmitate-17-propionate | 33.5 | 108*** | 43* | −1 (NS) | 2.0 (NS) |
| Flunisolide-21-palmitate | 33.5 | 133*** | 44 | 8 (NS) | −2.6 (NS) |
| Compounds for comparison | | | | | |
| Budesonide | 335 | 38 | 30 | — | 1.6 (NS) |
| Budesonide-21-valerate | 335 | 21 | 22 | −1 (NS) | −0.8 (NS) |
| Dexamethasone-21-palmitate | 335 | 127*** | 109*** | — | −10.8*** |
| Fluocinolone acetonide-21-palmitate | 100 | 117*** | 95*** | 15** | −4.8** |
| Hydrocortisone-21-palmitate | 335 | −13 | −7 | — | −1 (NS) |

NS = not significant
— = not investigated should have a very high glucocorticoid activity at the site of application in lung, but with low activity outside this area. Therefore, in the selected model an optimal preparation should more or less completely block the edema in the locally pretreated left lung lobe, but have much less activity in the right lung half and no significant inhibitory action on the spleen weight and the body weight gain. It has been considered more important to search for a high degree of separation between the local activity (exemplified with the left lung) to the other activities than to search for a high absolute potency (high activity per mg drug) for the action in the left lung. In the test protocol used, doses were selected leading to a more or less complete block of the edema in the left lung and at these dose levels the extent of the other activities was estimated. At the selected dose 7–9 rats were tested in parallel. Mean±s.e.m. was calcu-

What is claimed is:

1. A pharmaceutical composition for administration primarily to the respiratory tract comprising liposomes in combination with an antiinflammatory and antiallergic effective amount of a compound of the formula

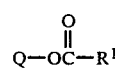

wherein Q is

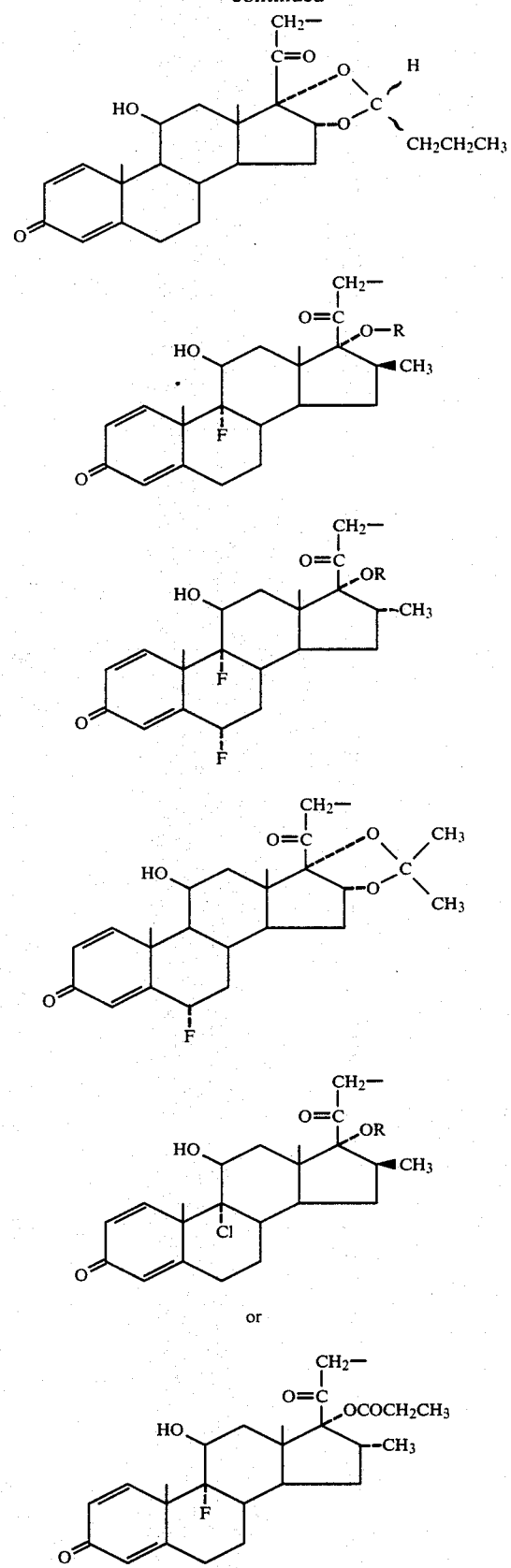

H, —COCH₃, —COC₂H₅, —CO(CH₂)₂CH₃ or —CO(CH₂)₃CH₃.

2. A composition according to claim 1 wherein the compound of formula I is

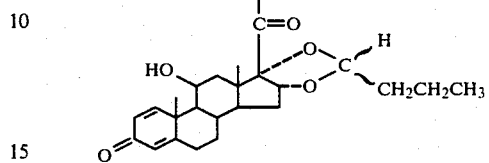

in the form of a stereoisomeric mixture or an epimer of the R or S type regarding the orientation of the substituents on the carbon atom at position 22.

3. A composition according to claim 1 which consists of a lyophilized liposome preparation containing a compound of the formula I.

4. A process for the preparation of a pharmaceutical composition according to claim 1 characterized in
   (a) dissolving a compound of the formula I defined in claim 1 and a lecithin in an organic solvent,
   (b) evaporating the solvent and thus obtaining the liposomes directly in an aqueous atmosphere, or
   (c) after evaporation, dispersing the lipid layers in an aqueous (with or without lactose) medium and
   (d) shaking or sonicating the obtained suspension or alternatively
   (e) drying of the liposome suspension.

5. A compound of the formula $$Q-O\overset{O}{\underset{\|}{C}}-R^1 \qquad I$$

wherein Q is

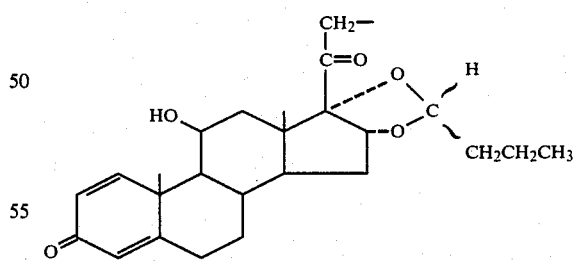

and R¹ is a saturated or unsaturated, straight or branched alkyl group with 11–19 carbon atoms and R is

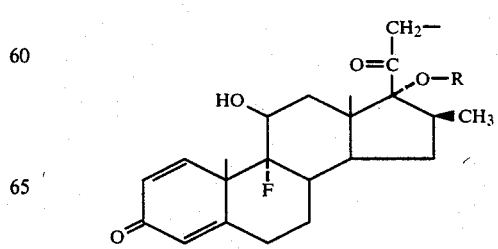

-continued

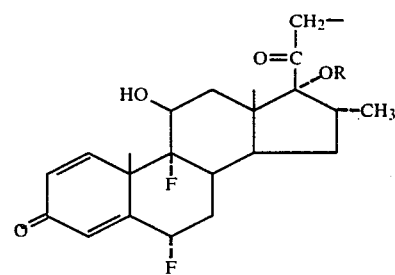

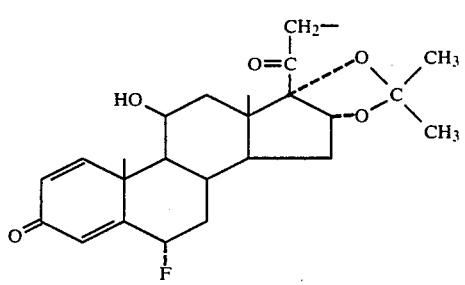

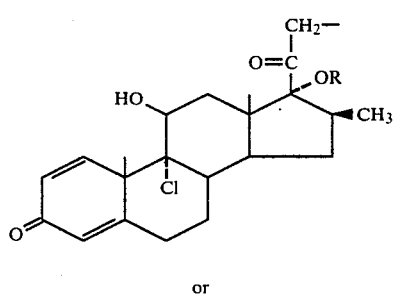

or

-continued

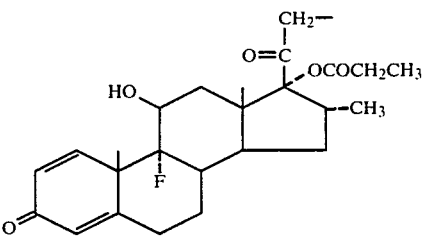

and $R^1$ is a saturated or unsaturated straight or branched alkyl group with 11–19 carbon atoms and R is H, —COCH$_3$, —COC$_2$H$_5$, —CO(CH$_2$)$_2$CH$_3$ or —CO(CH$_2$)$_3$CH$_3$.

6. A compound according to claim 5 wherein the compound of formula I is

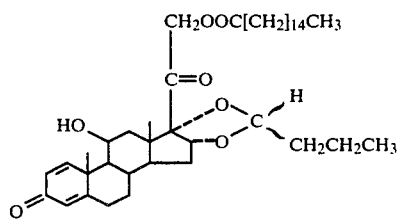

in the form of a stereoisomeric mixture or an epimer of the R or S type regarding the orientation of the substituents on the carbon atom at position 22.

7. A method for the treatment and control of inflammatory conditions in mammals, including man, characterized by the administration to a host in need of such treatment and effective amount of a composition according to claim 1.

* * * * *